US005378605A

United States Patent [19]
Feitelson et al.

[11] Patent Number: 5,378,605
[45] Date of Patent: Jan. 3, 1995

[54] METHOD OF DETECTING HEPATITIS B VARIANTS HAVING DELETIONS WITHIN THE X REGION OF THE VIRUS GENOME

[75] Inventors: Mark Feitelson, North Wales; Ling-Xun Duan; Jianhui Guo, both of Philadelphia, all of Pa.

[73] Assignee: Thomas Jefferson University, Philadelphia, Pa.

[21] Appl. No.: 74,346

[22] Filed: Jun. 8, 1993

[51] Int. Cl.$^6$ .................... C12Q 1/70; G01N 33/53; C12P 19/34
[52] U.S. Cl. .................... 435/5; 435/7.1; 435/7.92; 435/91.2
[58] Field of Search .......... 435/5, 7.1, 7.92, 91.2; 935/77, 78

[56] References Cited

U.S. PATENT DOCUMENTS 4,777,240 10/1988 Moriarty et al. ............ 530/326

OTHER PUBLICATIONS

Hilger et al., J. Virol. 65:4284–4291 (1991) "Diversity of hepatitis B virus X gene-related transcripts . . . ".
Okamoto et al., J. Gen. Virol. 69:2575–2583 (1988) "Typing hepatitis B virus by homology . . . ".
Feitelson et al., Virology 177:367–371 (1990) "X Antigen polypeptides in the Sera . . . ".
Bukh et al., Importance of Primer Selection for the Detection of Hepatitis C Virus RNA with the Polymerase Chain Reaction Assay, PNAS (USA), 89:187–191, 1992.
Feitelson et al., Presence of Antibodies to the Polymerase Gene Product(s) of Hepatitis B and Woodchuck Hepatitis Virus in Natural and Experimental Infections, J. Med. Virol., 24:121–136, 1988.
Feitelson et al., Hepatitis B X Open Reading Frame Deletion Mutants Isolated from Atypical Hepatitis B Virus Infections, J. Hepatology 13:S58–S60 (1991).
Feitelson and Clayton, Gastroenterol., X Antigen/Antibody Markers in Hepadnavirus Infections Antibodies to the X Gene Product(s), 99:500–507, 1990.
Figus et al., Hepatitis B Viral Nucleotide Sequences in Non-A, Non-B or Hepatitis B Virus-Related Chronic Liver Disease, Hepatology, 4:364–368, 1984.
Kaneko et al., Detection of Serum Hepatitis B Virus DNA in Patients with Chronic Hepatitis Using the Polymerase Chain Reaction Assay, PNAS (USA) 86:312–316, 1989.
Kaneko et al., Detection of Hepatitis B Virus DNA in Serum by Polymerase Chain Reaction, Gastroenterol. 99:799–814, 1990.
Liang et al., Characterization and Biological Properties of a Hepatitis B Virus Isolated from a Patient without Hepatitis B Virus Serologic Markers, Hepatology, 12:204–212, 1990.
Paterlini et al., Polymerase Chain Reaction to Detect Hepatitis B Virus DNA and RnA Sequences in Primary Liver Cancers from Patients Negative for Hepatitis B Surface Antigen, N. Engl. J. Med., 323:80–85, 1990.
Theirs et al., Transmission of Hepatitis B From Heaptitis-B-Seronegative Subjects, Lancet ii:1273–1276, 1988.
Tiollars, P., et al., The Hepatitis B Virus, 1985, Nature, 317:489–495.
Wands et al., Detection and Transmission in Chimpan- (List continued on next page.)

Primary Examiner—Margaret Parr
Assistant Examiner—Eggerton Campbell
Attorney, Agent, or Firm—Jane Massey Licata

[57] ABSTRACT

The present invention provides methods for the detection of hepatitis B virus in atypical infections by simultaneously detecting antibodies against the X and polymerase gene products of HBV. Further, the present invention provides methods for the detection of HBV in atypical infections in a polymerase chain reaction (PCR) assay employing selected primes. These primers allow the detection of a specific class of HBV variants. These methods are useful for demonstrating the presence of productive virus infection and may prove useful in monitoring therapeutics.

2 Claims, 4 Drawing Sheets

OTHER PUBLICATIONS zees of Hepatitis B Virus–Related Agents Formerly Designated "Non–A, Non–B" Hepatitis, *PNAS (USA)*, 79:7552–7556, 1982.

Wang et al. Detection of Hepatitis B Virus DNA by Polymerase Chain Reaction in Plasma of Volunteer Blood Donors Negative for Hepatitis B Surface Antigen, *J.*

Wang et al., Posttransfusion Hepatitis Revisited by Hepatitis C Antibody Assays and Polymerase Chain Reaction, *Gastroenterol*, 103:609–616, 1992.

Weiner et al., Detection of Hepatitis C Viral Sequences in Non–A, Non–B Hepatitis, *Lancet*, 335:1–3, 1990.

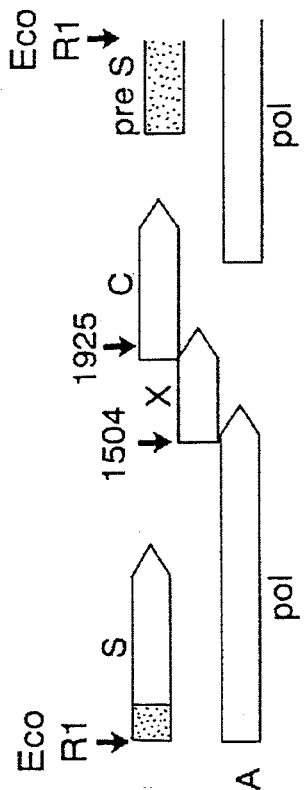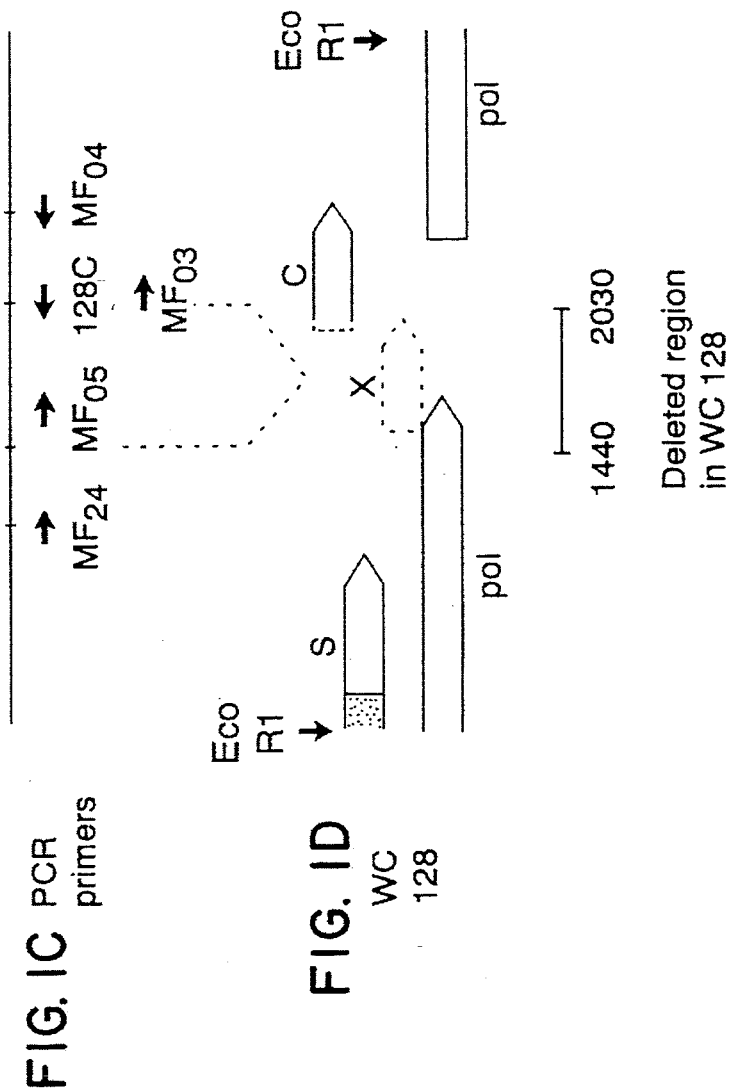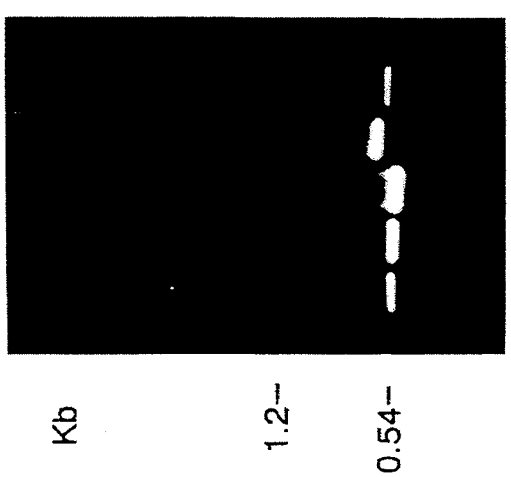

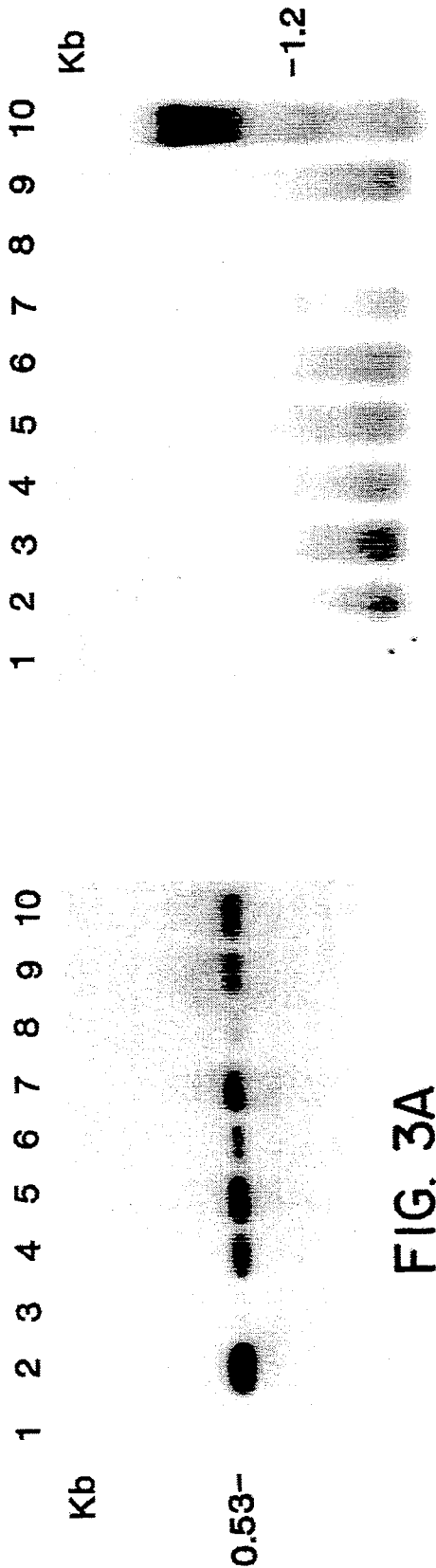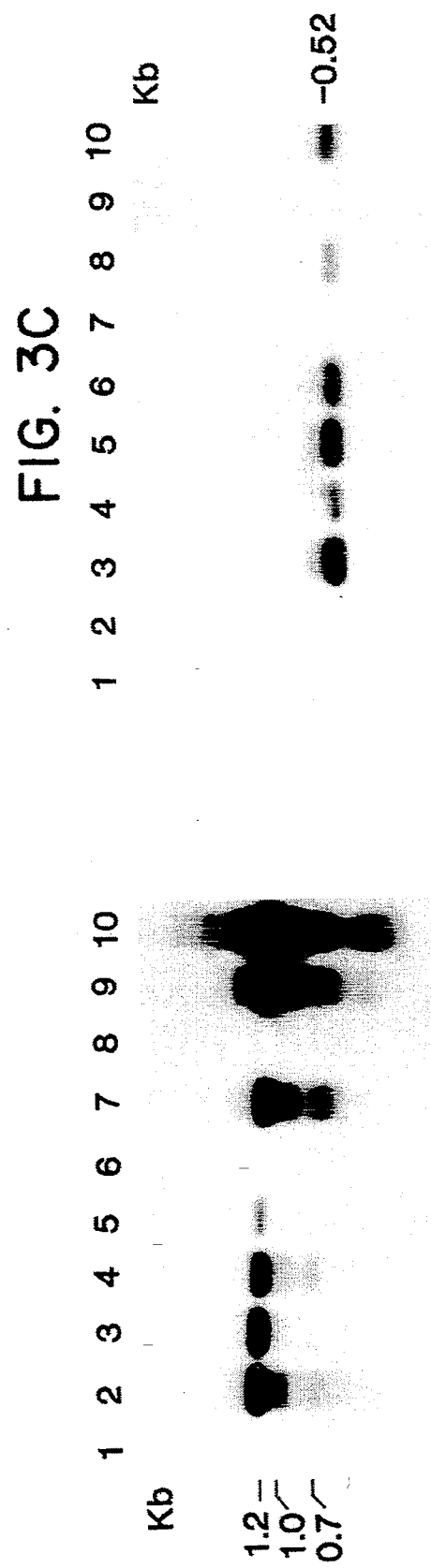

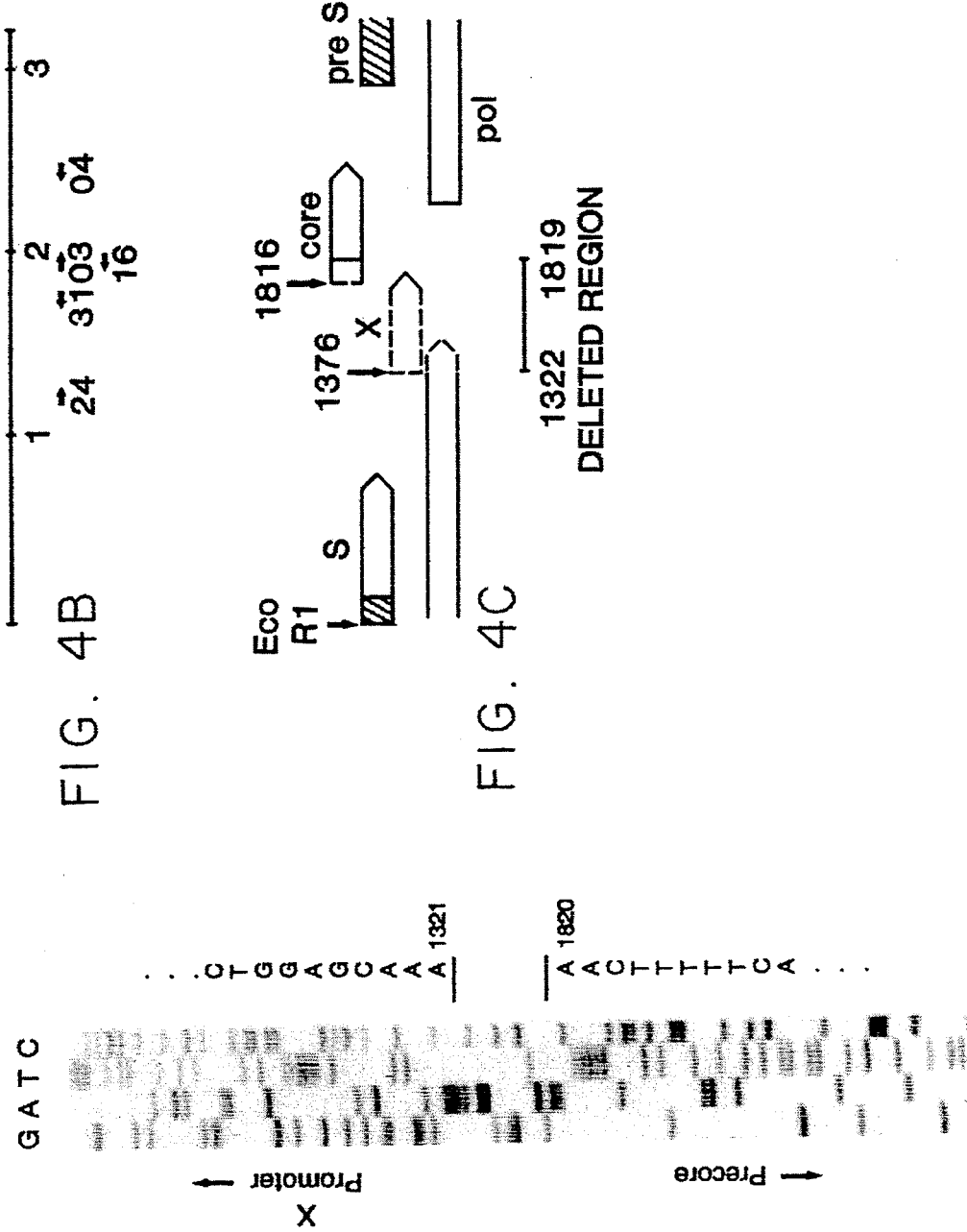

METHOD OF DETECTING HEPATITIS B VARIANTS HAVING DELETIONS WITHIN THE X REGION OF THE VIRUS GENOME

BACKGROUND OF THE INVENTION

The ability to eliminate posttransfusion hepatitis (PTH) and protect the blood supply worldwide depends upon the discovery and further characterization of the responsible virus agents. One of these agents, hepatitis B virus (HBV), is now eliminated from much of the blood supply by screening for the envelope antigenic determinants, or hepatitis B surface antigen (HBsAg), in serum. However, among three large prospective studies in which all blood samples were screened for HBsAg by radioimmunoassays, 0.3–1.7% of recipients of blood transfusions developed HBV, which accounts for 7–17% of PTH cases. These results demonstrate significant frequencies of PTH even with HBsAg screening. The association of antibodies against the hepatitis B core antigen (anti-HBc) with the transmission of HBV, and even more frequently with the transmission of non-A, non-B hepatitis (NANBH), suggests that HBV or a related agent present at low levels may contribute to PTH. The fact that only 2–9% of recipients of anti-HBc [+] blood develop posttransfusion hepatitis B, however, indicates that anti-HBc most often reflects past exposure and/or past infection. Rare cases of PTH have also been documented from blood with detectable antibodies against the hepatitis B surface antigen (anti-HBs), and studies have shown the presence of HBV DNA is serum samples from some anti-HBs [+] individuals by the highly sensitive polymerase chain reaction (Kaneko et al., *PNAS (U.S.A)* 86:312–316, 1989; Kaneko et al., *Gastroenterol.* 99:799–814, 1990). The finding of HBV DNA in HBsAg [−] cases of chronic liver disease underscores the need to find new ways to reliably detect and eliminate these types of HBV infections from the blood supply.

Another major cause of PTH is infection with HCV. Recently, serological assays have become available for the detection of HCV infections. Seroepidemiological data suggest that HCV accounts for the majority of PTH. It is estimated that roughly half of the patients infected with HCV develop chronic hepatitis, and that long term HCV infection is associated with the development of primary hepatocellular carcinoma (PHC). It has also been shown that one or more viral antibodies persist in patients who develop chronic infection. Many such patients also have persistent viremia, as shown by the detection of HCV RNA in serum by PCR (Wang et al., *Gastroenterol*, 103:609–616, 1992; Weiner et al., *Lancet*, 335:1–3, 1990; Bukh et al., *PNAS (U.S.A)*, 89:187–191, 1992). Evidence is also accumulating that continued HCV replication is associated with the development and progression of chronic liver disease. Research is now being carried out worldwide to elucidate the natural history of infection and the markers which will be best suited for the screening of donor blood for the presence of HCV.

Relatively rare causes of vital hepatitis result from infection with one or more herpesviruses. Human cytomegalovirus (HCMV), for example, has been reported to be associated with neonatal hepatitis, in patients with PTH associated with liver transplantation, and in a few percent of patients with sporadic hepatitis. Epstein Bart virus (EBV) has been found among patients with hepatitis following liver transplantation. Herpes simplex virus (HSV) is associated with hepatitis among immunosuppressed bone marrow recipients, even when the transplantation is autologous. Associations have also been shown between HSV and fulminant neonatal hepatitis and in acute hepatitis in adults. Despite the fact that herpesvirus associated hepatitis is rare, these vital etiologies need to be considered in blood screening when making a differential diagnosis of hepatitis.

The problems of PTH associated with HBV infection have been solved among the subset of potential blood donors who are asymptomatic but have detectable HBsAg in blood by current screening procedures. Clearly, a hallmark of chronic HBV infection is the variability in pathogenesis which accompanies such infections. Most people who become acutely infected with HBV resolve virus infection without the development of HBsAg, virus, or hepatitis. A small percentage develop fulminant hepatitis. Others develop acute hepatitis, followed by resolution in which HBsAg and HBV particles are cleared from the blood, followed by seroconversion to anti-HBs. Still others do not clear virus, but instead develop the chronic carrier state, which may be asymptomatic or may result in the appearance and progression of chronic hepatitis, cirrhosis, and eventually PHC. Among the more than 300 million estimated HBV carriers worldwide, at least 250,000 new cases of PHC are diagnosed annually; less than 3% of these patients survive 5 years. Given that the relative risk of HBV carriers developing PHC is more than 200:1, and that there are few treatments available for liver diseases associated with chronic HBV infection, including PHC, there is a real need to characterize HBV in HBsAg [−] infections from both the standpoints of screening and management.

While it has been suggested that the nature of the cellular and humoral immune responses against HBV are likely to be important to the outcome of acute infection, variation in the virus may also be very important to the host-virus relationship that evolves. To place this in context, while there are more than 300 million HBV carriers worldwide, it is estimated that about half of the world's population is infected with HBV but does not develop the HBsAg [+] carrier state.

U.S. Pat. No. 4,777,240 (Moriarty et al.) discloses methods for assaying for the presence of HBxAg and anti-HBx employing antigenic synthetic polypeptides. Preferred polypeptides have the following sequences:

Leu Ser Ala Met Ser Thr Asp Leu Glu Ala Tyr Phe Lys Asp (SEQ ID NO: 1);

Leu Phe Lys Asp Trp Glu Leu Gly Glu Ile Arg Leu Lys Val (SEQ ID NO: 2); and

Ala Pro Ala Pro Cys Asn Phe Thr Set Ala (SEQ ID NO: 3). Antibodies capable of reacting with one of the aforementioned antigenic polypeptides and a diagnostic assay system for determining the presence of a detectable amount of HBxAg in a body sample are also disclosed.

Assay systems are described. Such a system can include a first reagent containing receptor molecules that include an antibody combining site (such as antibodies) which is capable of reacting with a synthetic polypeptide of the invention. Indicating means such as a fluorescent dye, a radioactive element, or an enzyme-linked antibody raised to the first reagent's receptors are also provided. Such a reagent system is said to be useful for enzyme-linked immunosorbant assay (ELISA). Diagnostic assays employing anti-polypeptide receptor are also disclosed.

Methods for assaying for the presence of a detectable amount of HBxAg by admixing proteins from a body sample to be assayed with antibodies (receptors) capable of reacting with a synthetic polypeptide of the invention are also provided. The antibody may be labeled (radioactive or enzyme label) to signal an immunoreaction between HBxAg and the receptors. In these methods, the body sample is preferably bound to a solid matrix before being mixed with the receptors. The label may be a separate molecule or may be a part of the receptor.

These assay methods and systems are said to be useful for identifying the X protein in an ELISA or Western blot format.

In one example, serum from a patient diagnosed as having a hepatocellular carcinoma was found to contain antibodies that bound to one of the polypeptides of the invention.

Feitelson et al., *J. Hepatology* 13:S58-S60 (1991) showed HBV DNA in serum from HBsAg negative renal dialysis patients by polymerase chain reaction (PCR) employing the following primers: MF03 (residues 1903-1929) and MF04 (residues 2436-2412) for amplification of the core region; MF24 (residues 1231-1247) and MF04 for amplification of the X plus core region; MF16 (residues 1929-1903; complementary to MF03) and MF24, for amplification of the X region; MF06 (residues 2850-2873) and MF07 (residues 154-132) for amplification of the preS region. The HBV-DNA and clone numbering system is used to designate the residues. The clone used was ayw; position 1 is at the Eco R1 site in HBV DNA (Tiollars, P., C. Pourcel, A. Dejean, 1985*Nature*, 317:489-495).

It was found that there detectable X deletion mutants months or years before the appearance of HBsAg and wild-type HBV-DNA in serum, suggesting that these mutant strains could infect liver and replicate at low levels relative to wild type. Virus particles carrying different X region deletion mutations were found in a single infection. Results also indicated that patients could be infected with different X deletion mutants while on dialysis and/or that two or more mutants may undergo genetic recombination.

Similar results in WHV-infected woodchucks are also discussed. Among infected individuals in which only X region deletion mutants are present in serum, most with detectable X antigen in serum are also positive for surface antigen, anti-core, and virus DNA. In contrast, those without evidence of X polypeptide production are usually negative for surface antigen, anti-core and virus DNA by conventional techniques. Some in the latter group have detectable anti-pol as the only serological marker of infection.

Perhaps the most challenging problem in HBV associated PTH is to find ways of detecting HBV transmission in blood lacking all serological markers of infection. This is important because there is growing evidence that HBV transmitted in blood lacking all conventional markers of infection. It has been shown that HBV DNA sequences are detectable in the serum (Theirs et al., *Lancet* ii:1273-1276, 1988; Wang et al., *J. Infect. Diseases*, 163:397-399, 1991) and liver (Figus et al., *Hepatology*, 4:364-368, 1984; Paterlini et al., *N. Engl. J. Med.*, 323:80-85, 1990) of patients without other HBV markers. An anti-HBs-like monoclonal antibody has been developed to detect such agents by immunoprecipitation. The agent binding to this antibody has been shown to transmit hepatitis in chimpanzees (Wands et al., *PNAS (U.S.A.)*, 79:7552-7556, 1982). However, there remains a need for methods capable of detecting active HBV infection, characterizes by virus replication, in HBsAg [−], anti-HCV [−] PTH.

SUMMARY OF THE INVENTION

The present invention provides methods for the detection of hepatitis B virus (HBV) in atypical infections by simultaneously detecting antibodies against the X and polymerase gene products of HBV. These antibody specificities are referred to as anti-HBx (antibodies against the hepatitis B X antigen (HBxAg) encoded by HBV) and anti-pol (antibodies against polymerase (pol) of HBV). Such methods are provided to reduce post-transfusion hepatitis (PTH) due to hepatitis B.

Further, the present invention provides methods for the detection of HBV in atypical infections in a polymerase chain reaction (PCR) assay employing selected primers. These primers allow the detection of a specific class of HBV variants. Such methods are useful for demonstrating the presence of productive virus infection and may prove useful in monitoring therapeutics.

DESCRIPTION OF THE DRAWINGS

FIG. 1 provides definition of the X deletion mutant in WHV particles from woodchuck 128. Panel A: PCR amplification of paired liver and serum samples from woodchuck 128. Amplification was carried out using primers MF03 and MF04 (for the core region (0.54 kb) and primers MF24 and MF04 (for the X plus core region; 1.2 kb). Lanes 1-3: core region amplification. Lane 1: WHV DNA from liver; Lane 2: WHV DNA from serum; Lane 3: core region amplified from, WHV DNA containing plasmid. Lanes 4-6: X plus core region amplification. Lane 4: WHV DNA from liver; Lane 5: WHV DNA from serum; Lane 6: X plus core region amplified from WHV DNA containing plasmid. Note that the core region is the expected size from virus in serum but that the X plus core region is considerably smaller than expected. Panel B: Schematic representation of the ORFs in wild type (wt) WHV DNA linearized at the Eco R1 site. Panel C: PCR primers used for amplification of the core and X plus core regions. Panel D: Schematic representation of the deleted region of WC 128 WHV DNA (dashed lines) as determined by DNA sequence analysis. To obtain this sequence, the PCR products were cloned into pGEM 3Z or 4Z plasmids and analyzed by dideoxy sequencing.

FIG. 3 shows the results of Southern blot hybridization of the core, X, and X plus core regions from the sera of patients with different types of HBV infections. In each panel, serum from 10 patients (on renal dialysis or thalassemia) were PCR amplified, and the products analyzed by agarose gel electrophoresis. Southern blotting was carried out using a core region probe (Panels A–C) or an X region probe (Panel D) labeled with fluorescein-conjugated dUTP by random priming. After hybridization and washing under stringent conditions, the signals were detected by addition of horse radish peroxidase (HRP) conjugated anti-fluorescein antibody and ECL substrate (Amersham). Panel A: PCR amplification of the core region of HBV DNA. Lanes 2–6 are from HBV carriers; lanes 1 and 7 –10 are from HBsAg [−] patients with anti-HBs and/or anti-HBc (lanes 1, 7 , and 8) or with unexplained elevated alanine aminotransferase (ALT) (lanes 9 and 10). Panel B: PCR amplification of the X plus core region from HBsAg [+] serum samples. Note the presence of the expected 1.2 kb band in most patients, and the variable presence of faster migrating bands, consistent with the presence of deletions in the x/preC region, among some patients. Panel C: PCR amplification of the X plus core region from HBsAg [−] serum samples. Note the presence of a faint band at 1.2 kb in some patients, and the presence of a faster migrating hybridizable smear in most patients, which is consistent with the presence of variably sized X/preC deletions. Panel D: PCR amplification of the X region from HBV DNA. Note that the X region sequences spanning one or both primers chosen for amplification appear to be missing in some cases, resulting in no PCR product which may indicate one or more mutations within the X region.

FIG. 4 shows the DNA sequence analysis of one clone from a patient with β-thalassemia. A. Sequence ladder including deletion. Note that the deletion in this clone spans some of the X promoter/enhancer complex (bases 1322–1375 deleted), most of the X region (bases 137 6–1820 deleted; the X gene terminates at base 1838) and the pre C translation initiation codon (at position 1816). The point of deletion contains 12 bases whose origin is unknown. B. Schematic diagram of the region showing the deleted sequences (dashed lines).

DETAILED DESCRIPTION OF THE INVENTION

Figure 2A:
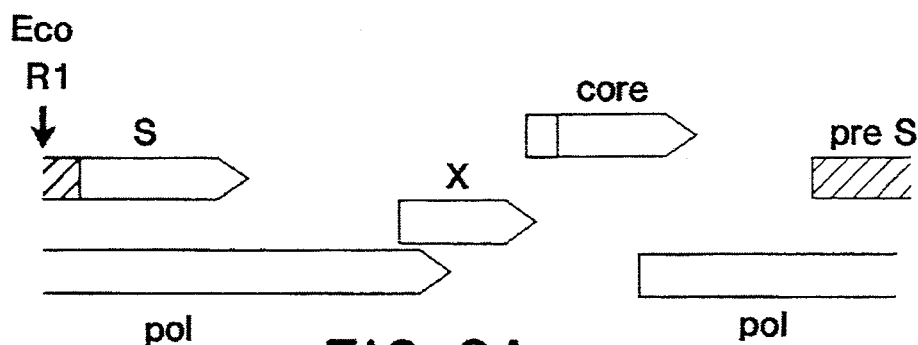
FIG. 2 shows the results of PCR amplification of the X plus core region of HBV DNA in sera from patients with different types of HBV infection. DNA was extracted from sera, and amplified for 35 cycles using 1 unit of Taq polymerase/reaction. After amplification, results were analyzed by agarose gel electrophoresis and ethidium bromide staining. The topology of the HBV DNA ORFS (Panel A) relative to the primers used for PCR amplification (Panel B) and the expected sizes of the amplified products (Panel C) are presented together on the left hand side of the figure. Panel D: Ethidium bromide stained gel from the following samples: Lane 1: Hind III digested fragments of λ-DNA. Lane 2: expected size X plus core region (1.2 kb) amplified from wt HBV DNA cloned into pBR322. Lanes 3-5: serum samples from HBsAg [−] patients with anti-HBs and/or anti-HBc. Lane 6: serum sample from an anti-HBe [+] HBsAg carrier. Lanes 7 and 8: serum samples from two HBeAg [+] HBsAg [+] carriers.

The variability in pathogenesis of HBV infection among different patients may be attributed, in part, to the appearance of HBV mutants. The presence of such mutants may contribute to the persistence of chronic HBV infection even in patients who have eliminated wt HBV, while infection with such mutants may lead to atypical HBV infections in which the expected serology, i.e., HBV antigens or corresponding antibodies, is not present. The latter situation represents an important problem in the screening of blood for HBV. Transmission of such mutants may be responsible for the persistence of PTH even with all of the current assays for HBV and HCV in common practice. The presence of HBV DNA by PCR in many HBsAg [−] , anti-HBs [+] patients is consistent with the presence of virus mutants . The appearance of these variants during natural infection or after interferon therapy, suggests that such mutants may significantly alter the pathogenesis of chronic infection. In addition, there appears to be a difference in the type of hepatitis resulting from acute infection with wt compared to some mutant HBVs; wt infections give rise to acute hepatitis while mutants have been found associated with fulminant hepatitis.

The patterns of two antibody makers associated with HBV infection have now been identified. These antibodies are against the polymerase of HBV (anti-pol) and against t,he HBxAg polypeptide (anti-HBx). (Liang et al Hepatology, 12:204–212, 1990; Feitelson et al., J. Med. Virol, 24:121–136, 1988). It is known that HBxAg and the virus polymerase are the major components associated with the replication complex of HBV so that the corresponding antibody responses reflect virus replication in an infected host. It is also known that viral replication occurs within subviral nucleocapsid particles in the cytoplasm of infected cells. It is believed that the submembranous or membranous localization of some of these nucleocapsid or core particles could provide stimulus for the generation of one or more immune responses against components of the replication complex. Anti-pol appears many weeks to months prior to the first appearance of HBsAg among infected patients . For example, anti-pol has been found in serum samples from renal dialysis patients during the incubation phase of HBV infection. The incubation period of infection is also characterized by intrahepatic HBV replication, and it is believed that the very early anti-pol response observed in such patients reflects HBV replication in the liver even though markers of virus replication in serum appeared at a later time. Anti-pol appears to reflect intrahepatic HBV replication in the absence of any other serological marker of infection.

In contrast, there was an inverse correlation between the appearance of anti-HBx in HBsAg [+] patients and the detection of wt HBV DNA by dot blot hybridization in serum. The appearance of anti-HBx and corresponding loss of HBV DNA may indicate that anti-HBx and/or immune responses associated with it are responsible, at least in part, for clearing of the virus from serum. Since HBxAg polypeptides are associated with the replication complex of the virus, it is not likely that they are exposed to corresponding antibodies in intact, enveloped virion particles. Therefore, the reduction in the serum levels of HBV may reflect elimination of hepatocytes with high levels of replication complexes. The appearance of anti-HBx near the time of chronic infection, which is characterized by an acute exacerbation in chronic Liver disease, due to removal of cells replicating virus, is also consistent with this. Therefore, it was surprising to find anti-HBx and/or anti-pol in serum samples from patients diagnosed as having NANBH since it suggested that they were infected with HBV. Further characterization of the antibody positive patients for HBV DNA by PCR using a variety of primer pairs showed that anti-HBx and anti-pol did, indeed, reflect underlying HBV infection. Closer examination showed that the HBV was not wt DNA, and in fact represented a new class of mutants with apparent deletions within the X region of the virus genome. This class of mutants is believed to be responsible for unexplained hepatitis in renal dialysis patients negative for HBsAg, anti-HBs, anti-HBc, anti-HAV and anti-HCV. The presence of this mutant class in 13 of 14 children tested with β-thalassemia suggests that these variants are passed by transfusion of Red Cross screened blood. Therefore, the methods of the present invention would be useful for determining the presence, frequency and distribution of these mutants in serum samples of populations at high risk for the development of PTH. These methods will allow the efficacy of virus inactivation protocols to be evaluated (which is paramount for providing safe pooled blood fractions for distribution) and intervention protocols among infected patients to be properly interpreted. In addition, the fact that such mutants are associated with HBsAg [−] chronic infection suggests approaches for treatment of HBsAg [+] carriers which could result in the termination of the HBsAg [+] carrier state, with a reduction in the risk for the development of PHC.

A class of viral mutants having deletions in the X region were first discovered in woodchucks infected with a hepatitis B-like virus. This agent, called woodchuck hepatitis virus (WHV) has many of the same biological characteristics as HBV. However, WHV infections are generally more productive (i.e., make more virus) than HBV infections. The amino terminal 20 residues of woodchuck hepatitis x antigen (WHxAg) polypeptide was sequenced and compared with viral DNA from the serum of the animal. When the X region of WHV was PCR amplified with different sets of primers, no product was observed after agarose gel electrophoresis and ethidium bromide staining. When primers spanning the X plus core regions were used for PCR amplification, a smaller than expected band was observed (shown in FIG. 1). Amplification of the core gene yielded the expected sized band. This result suggested a deletion in the X region of WHV DNA. The extent of this deletion was defined by cloning and sequencing of viral DNA from serum. To exclude cloning artifacts, direct sequencing of the PCR amplified band from serum was carried out. Direct cloning and sequencing (without a PCR step) was also successful, suggesting that the deletion observed did not arise in the course of PCR amplification. These results showed the existence of a new class of virus mutants with large deletions in the X/ pre-core (preC) region of the genome.

When the X plus core region was PCR amplified from an infected woodchuck liver, partially truncated X regions were observed (shown in FIG. 1) PCR amplification of the X region also showed bands compatible with the presence of X deletion mutants. These results show that some WHV infections replicate defective particles with large deletions in the X ORF.

Figure 2B:
Figure 2C:
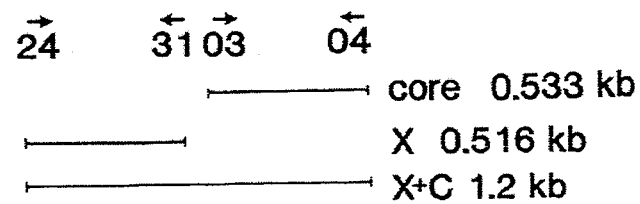
Figure 2D:
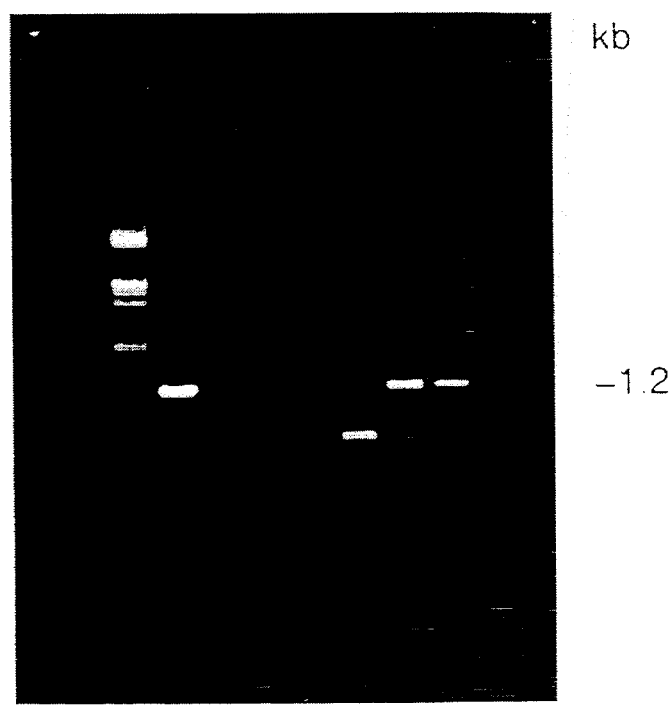

Deletion mutants in HBV infections were also found using primers MF04 and MF24, which amplify the X plus core region. A 1.2 kb band was observed after PCR amplification of serum samples from HBeAg [+] carriers (shown in FIG. 2, lanes 7 and 8). However, smaller than expected bands were observed following amplification of serum samples from some anti-HBe [+] HBsAg carriers (shown in FIG. 2, lane 6) and from HBsAg [−] patients with anti-Hbs and /or anti-HBc (shown in FIG. 2, lanes 3-5). Amplification of the core region along with MF03 and MF04 from these same sera yielded only a single band at the expected size, suggesting a wt core region. The availability of serial serum samples collected over 2-10 years from renal dialysis patients were used to determine the presence, frequency and distribution of the putative X mutants. These mutants were detected in HBsAg [−] serum samples obtained from renal dialysis patients who later developed the HBsAg [+] chronic carrier state and reappeared in some of the same carriers years after the appearance of HBsAg (shown in Table 1). The mutants also appeared in the serum from carriers after seroconversion from HBeAg to anti-HBe (shown in Table 1). Among patients who were transiently HBsAg [+], X mutants were detected after the clearance of HBsAg and appearance of anti-HBs. Most of the HBV infected patients who had viral antibodies (anti-HBs and/or anti-HBc) as the only markers of infection had X mutants in most of their serum samples collected over time. The same trend was observed among patients who had elevated ALT, but no markers of HBV infection (shown in Table 1).

TABLE 1

FREQUENCY OF X REGION MUTANTS IN RENAL DIALYSIS PATIENTS WITH DIFFERENT TYPES OF HBV INFECTIONS

| | Patient Category[a] | | | | |
|---|---|---|---|---|---|
| | 1 | 2 | 3 | 4 | 5 |
| X region | | | | | |
| wild type cases/total | 4/8 | 1/8 | 2/7 | 1/7 | 0/8 |
| % | 50 | 12 | 29 | 14 | 0 |
| mutant cases/total | 4/8[b] | 7/8[c] | 5/7[d] | 6/7 | 8/8 |
| % | 50 | 88 | 71 | 86 | 100 |

[a]The patient categories listed are as follows: 1) chronic carriers, HBeAg persistent; 2) chronic carriers, HBeAg to anti-HBe seroconversion; 3) acute infection, transient HBsAg; 4) antibody only (no virus antigens in serum) (anti-HBs, anti-HBc and/or anti HBe); 5) ALT peak only (no other virus markers in serum).
[b]In this group, 3 patients had X mutants in HBsAg serum samples; 1 at the peak of virus replication (+3 months after the appearance of HBsAg), 3 patients had X mutants 3 years after the appearance of HBsAg, and 3 patients had X mutants in HBxAg [+] serum. Two in the latter group developed X mutants years after the establishment of the chronic carrier state.
[c]In this group, at least 5 patients had X mutants in HBsAg [−] serum samples, 1-2 at the peak of HBV replication, and at least 5 developed X mutants years after seroconversion to anti-HBe.
[d]In transiently infected patients, 2 had definitive evidence of x mutants prior to the appearance of HBsAg, 2 had X mutants within the HBsAg peak, and at least 4 had X mutants after clearance of HBsAg.

Hence, most of the serum samples with X mutants were HBsAg [−]. Further, the mutants were present in a larger proportion of the serum samples from patients with the fewest markers of HBV infection.

The patients with the fewest serological markers of typical HBV infection were those with the highest frequency of X mutants, which reflects the different host-virus relationships that evolve from infections from such mutants. The fact that anti-pol and anti-HBx assays signaled the presence of X mutants in many renal dialysis patients with unexplained elevated transaminases (many were anti-HCV [−]), and that HBV infections in many were confirmed by PCR (shown in Table 2), may indicate that these mutants may contaminate renal dialysis units and infect a large proportion of patients sharing the same facility (shown in Table 3). The results also show that the methods of the invention definitively identify the etiology of PTH in patients with unknown cause as well as assist in the differential diagnosis of PTH (as shown in Table 3).

TABLE 2

PRESENCE OF HBV IN RENAL DIALYSIS PATIENTS WITH ABNORMAL ALT

| Patient 1: | | | | | | | | | | | |
|---|---|---|---|---|---|---|---|---|---|---|---|
| HBsAg | − | − | − | − | − | − | − | − | − | − | − |
| anti-HBs | − | − | − | − | − | − | − | − | − | − | − |
| anti-HBc | − | − | − | − | − | − | − | − | − | − | − |

TABLE 2-continued

PRESENCE OF HBV IN RENAL DIALYSIS PATIENTS WITH ABNORMAL ALT

| | | | | | | | | | | | | | |
|---|---|---|---|---|---|---|---|---|---|---|---|---|---|
| anti-pol | − | − | − | − | − | + | + | + | − | − | + | + | |
| anti-HBx | − | + | + | − | + | + | + | + | + | + | + | + | |
| anti-HCV* | − | − | − | − | − | − | − | − | − | − | − | − | |
| HBV DNA: | | | | | | | | | | | | | |
| dot blot | − | − | − | − | − | − | − | − | − | − | − | − | |
| PCR | − | + | + | + | + | − | + | + | + | + | + | + | |
| ALT | 19 | 79 | 22 | 24 | 15 | 90 | 87 | 76 | 38 | 25 | 53 | 10 | |
| months | 0 | 2 | 4 | 6 | 8 | 10 | 12 | 14 | 17 | 19 | 21 | 25 | |
| Patient 2: | | | | | | | | | | | | | |
| HBsAg | − | − | − | − | − | − | − | − | − | − | − | − | − | − |
| anti-HBs | − | − | − | − | − | − | − | − | − | − | − | − | − | − |
| anti-HBc | − | − | − | − | − | − | − | − | − | − | − | − | − | − |
| anti-pol | − | − | − | − | − | + | + | + | − | + | − | − | + | − |
| anti-HBx | − | − | − | − | − | − | − | − | − | − | − | − | − | − |
| anti-HCV* | − | − | − | − | − | − | − | − | − | − | − | − | − | − |
| HBV DNA: | | | | | | | | | | | | | | |
| dot blot | − | − | − | − | − | − | − | − | − | − | − | − | − | − |
| PCR | − | − | − | − | + | − | + | + | − | − | − | − | | |
| ALT | 16 | 12 | 5 | 72 | 13 | 213 | 156 | 105 | 85 | 95 | 90 | 77 | 75 | 75 |
| months | 0 | 4 | 9 | 13 | 17 | 20 | 24 | 28 | 37 | 42 | 45 | 48 | 51 | 55 |
| Patient 3: | | | | | | | | | | | | | | |
| HBsAg | − | − | − | − | − | − | − | − | − | − | − | − | | |
| anti-HBs | − | − | − | − | − | − | − | − | − | − | − | − | | |
| anti-HBc | − | − | − | − | − | − | − | − | − | − | − | − | | |
| anti-pol | − | − | − | − | − | − | − | − | − | − | − | − | | |
| anti-HCV* | − | − | − | − | − | − | − | − | − | − | − | − | | |
| HBV DNA: | | | | | | | | | | | | | | |
| dot blot | − | − | − | − | − | − | − | − | − | − | − | − | | |
| PCR | − | | − | | + | | + | | − | | | | | |
| ALT | 13 | 5 | 147 | 49 | 10 | 18 | 8 | 0 | 18 | 15 | 28 | 21 | 15 | |
| months | 0 | 8 | 9 | 10 | 12 | 13 | 15 | 16 | 17 | 18 | 19 | 20 | 21 | |

These results show that HBV DNA could be detected by PCR in patients with unexplained liver tisease, and that in many cases, the appearance of HBV DNA is accompanied by a peak of transaminases (ALT) and anti-HBx and/or anti-pol.
*The anti-HCV antibodies were detected by the second generation ELISA.

TABLE 3

ORIGIN OF HEPATITIS IN RENAL DIALYSIS PATIENTS TESTING NEGATIVE FOR HBSAG AND ANTI-HBs

| No. of Patients | HBV DNA$^a$ | anti-HBx$^b$ | anti-pol$^b$ | anti-HCV$^c$ | interpretation (infection type) |
|---|---|---|---|---|---|
| 3 | + | + | + | − | HBV |
| 3 | − | + | + | − | HBV |
| 3 | + | − | + | + | HBV + HCV$^d$ |
| 2 | + | + | − | − | HBV |
| 4 | − | + | − | + | HBV + HCV$^e$ |
| 3 | + | + | + | + | HBV + HCV$^f$ |
| 2 | + | − | + | − | HBV |
| 4 | + | − | − | + | HBV + HCV$^g$ |
| 3 | + | − | − | − | HBV$^h$ |
| TOTALS | | | | | |
| 32 | 25 | 15 | 18 | 14 | | between HBV and liver disease in 14 of the 32 patients studied (44%).

Legend to Table 3

HBV DNA was determined by PCR amplification of the core gene using primers MFO3+MFO4. Anti-HBx and anti-pol ere measured by specific ELISAs using known techniques.

Anti-HCV antibodies were detected using the second generation ELISA (Abbott Labs.) All 3 of these patients developed anti-HCV simultaneously or just after the rise in ALT, suggesting that liver damage was associated with HCV infection. Three patients in this category developed anti-HCV simultaneously or just after the rise in ALT, suggesting that liver damage was associated with HCV infection. The remaining patient had anti-HCV prior to the rises in ALT, suggesting on going HCV infection. The latter patient developed anti-pol prior to the ALT peak, and anti-HBx after the rise in ALT, implying that replication of HBV was associated with liver damage in this patient.

One patient in this category developed anti-HCV just after the rise in ALT, suggesting that liver damage was associated with HCV infection. Two more patients had anti-HCV prior to the rises in ALT, suggesting on going HCV infection. The latter 2 patients also developed HBV DNA by PCR just after the ALT peak, as well as anti-HBx in these individuals.

Three patients in this category developed anti-HCV simultaneously with the rise in ALT, suggesting that liver damage was associated with HCV infection. The other patient had detectable anti-HCV prior to the ALT peak, and at or after the peak, HBV DNA became detectable by PCR. This suggests that the liver disease in the latter patients was associated with HBV infection.

The ALT peak(s) in this group correlated with the appearance of HBV DNA, as it did in 6 patients with mixed infections above, suggesting an association between HBV and liver disease in 14 of the 32 patients studied (44%).

The detection of X mutants in the blood of patients with unexplained hepatitis indicated that such mutants may be transmitted through Red Cross screened blood and pooled blood fractions. Serum samples from 14 children with β-thalassemia were screened for these mutants (shown in Table 4).

Serum was collected from these patients in 1981 and, since all were anti-HBs [−], they were given the HBV vaccine in 1983. Each of these children developed anti-HBs after vaccination, which was still detectable in 1989. Eleven of the 14 children developed one or more episodes of hepatitis from 1981–1989. Half of the children were anti-HCV [+] in 1981 but by 1989, all were positive. In 1981, 11 of the children were anti-HBx [+] and all 14 were anti-pol [+] indicating HBV infection (shown in Table 4).

TABLE 4

| PRESENCE OF X MUTANTS IN CHILDREN WITH β-THALASSEMIA | | | | | |
|---|---|---|---|---|---|
| | anti-HBs+ | anti-HBx+[b] | anti-pol+[b] | anti-HCV+[c] | core PCR+[d] | X + core PCR+[d] |
| vaccination status[a] | | | | | | |
| before 1981 | 0 | 11 | 14 | 7 | 5 | 7 |
| after 1989 | 14 | 2 | 5 | 14 | 9 | 11 |

[a]With regard to vaccine status, the first sample from each case was acquired before vaccination in the year indicated. The second sample from each case was acquired several years after vaccination (i.e., after 1983) during the year indicated.
+[b]Anti-HBx and anti-pol assays were carried out according to published criteria (Feitelson et al., J. Med. Virol., 24:121-136, 1988; Feitelson and Clayton, Gastroenterol., 99:500-507, 1990).
+[c]Anti-HCV was determined using the commercially available second generation assay.
+[d]For PCR using the core primers, a positive [+] result indicates the presence of the expected sized band for the amplification product on agarose gels, while a negative signal indicates that no band was observed by Southern blotting. For PCR using the primer pair which amplifies the X + core region, a positive [+] result indicates the presence of one or more bands which confirmed to be HBV DNA by Southern blot hybridization.

Productive HBV infection was confirmed in 8 cases by PCR. By 1989, only 2 children were anti-HBx [+] and anti-pol [+], respectively. Thirteen of the 14 children were PCR positive for the core or the X plus core regions. These results suggest that thalassemic children are commonly infected with the X mutant strains of HBV, and that such mutants are being missed by the available screening methods for wt HBV.

The nature of the bands resulting from PCR amplification were determined by Southern blot hybridization (shown in FIG. 3). Panel A shows the results from PCR amplification of the core region from some of the renal dialysis and thalassemia patients. A single band, at the expected size, hybridizes with the core probe, verifying that these patients are infected with HBV. PCR amplification of the X plus core region among HBsAg [+] renal dialysis patients (Panel B) results in the expected size of 1.2 kb in most cases, but also yields a number of faster migrating bands, consistent with the presence of variably sized X deletions in some of these individuals. When X plus core PCR amplification is carried out using serum samples from HBsAg [−] patients, little or no 1.2 kb product is observed (Panel C). Instead, a smear of faster migrating species, which may represent variably sized deletions in the X/preC region, is observed. If the faster migrating bands (Panel B) or smear (Panel C) represent a family of different sized X deletion mutants, then there are far fewer mutants in HBsAg [+] compared to HBsAg [−] patients. PCR amplification of several sera from HBsAg [−] patients with X region primers (M24 and M31; see FIG. 2) show that in some patients the wt sized X region appears to be present (FIG. 3; Panel D), while in other patients, there appears to be no evidence for the presence of wt HBV (e.g., lanes 1, 2, 7, and 9). Together, these results indicate the existence of heterogeneity within the X region of HBV DNA derived from natural infections characterized by atypical (anti-HBx and/or anti-pol) or no HBV serology.

The presence of HBV DNA in serum samples from NANB patients and from apparently uninfected populations was evaluated. The results are shown in Table 5.

TABLE 5

| no. | anti-HBX | anti-pol | core region PCR |
|---|---|---|---|
| | tested[a] | (ELISA) | (ELISA) | (primers 03 + 04) |
| NIH panel[b] | | | | |
| proven NANBH | 8 | 4 (50%) | 1 | 4 (50%) |
| normal donors | 5 | 0 | 0 | 1 (20%) |
| biliary cirrhosis | 1 | 0 | 0 | 0 |
| alcoholic hep. | 1 | 0 | 0 | 1 |
| FCCC[c] | | | | |
| proven NANBH | 8 | 3 (38%) | 2 (25%) | 5 (62%) |
| normal donors | 14 | 0 | 0 | 0 |
| Japanese | | | | |
| proven NANBH | 140 | 25 (18%) | 18 (13%) | 42 (30%) |
| Red Cross | | | | |
| normal donors | 156 | 7 (4,5%) | 6 (3,8%) | 8 (5%) |
| Biliary cirrhosis | 132 | 3 (2.3%) | 4 (3%) | 5 (3.8%) |
| Asian immigrants | 170 | 9 (5.3%) | 4 (2.4%) | 8 (4.7%) |

[a]All individuals tested here were seronegative for HBsAg, anti-HBs and anti-HBc.
[b]The NIH panel used were serum samples from post-transfusion NANB hepatitis patients and controls. Proven NANBH = liver biopsy cont irmed in this and the other groups of patients listed in the table.
[c]Samples obtained from the Fox Chase Cancer Center. The normal donors in this group were individuals from other laboratories with no evidence of HBV infection or history of liver disease.

Note the presence of anti-HBx, anti-pol, and/or the expected HBV DNA core region PCR product in many serum samples from populations with NANB hepatitis. This finding suggests that HBV is present in a substantial number of patients diagnosed as having NANBH. Amplification of the X plus core region from these patients yielded a smear of radioactivity ≦1.2 kb. These results suggest the presence of variably sized X deletion mutants in NANBH serum samples. Similarly, the finding of X deletion mutants in 2-5% of different populations at low risk for the development of post-transfusion NANB hepatitis (e.g., Red Cross donors, patients with biliary cirrhosis, and Asian immigrants to the greater Philadelphia region) suggests that a considerable reservoir of these mutants exists in the general population. The percentages are at least as large as those for HCV, which is now being screened for worldwide. Combined with the observations that most thalassemic children with post-transfusion hepatitis are infected with both HCV and the X deletion mutants (Table 4), the results suggest the transmission of X deletion mutants at high frequency to individuals multiply transfused by Red Cross screened blood. This implies contamination of the blood supply by HBV variants which are not screened out by current commercially available technology. The fact that these mutants are still detected in serum samples of thalassemic children years after successful HBV vaccination makes an even stronger case for screening blood for X deletion mutants using the assays within the patent application, since vaccination may not protect against infection by these HBV variants. In addition, the finding that renal dialysis patients with elevated transaminases and testing negative for anti-HCV by the second generation assay appear to become infected with X deletion mutants of HBV (FIG. 3C and Table 2) indicates that the methods of the invention for detecting the X deletion mutants will be very useful in the diagnosis of NANBNC hepatitis.

The invention is further illustrated by the following, non-limiting examples.

EXAMPLES

Example 1 Polymerase Chain Reaction

PCR is carried out using primer pairs which amplify different regions of HBV DNA. The first pair used for amplification spans the core gene of HBV (subtype adw; 69). Primer MF03 covers nucleotide bases 1903–1949, inclusive, at the beginning of the core open reading frame (ORF), and has the following sequence: 5'ATGGACATCGACCCTTATAAAGAATTTG3' (SEQ ID NO: 4). Primer MF04 covers nucleotide bases 2436–2412, inclusive, near the end of the core ORF, and has the following sequence: 5'CTAAGATTGAGATCTTCTGCGACGCGG3' ( SEQ ID NO: 5) . The second pair used for amplification spans the core plus X regions of HBV DNA. MF04 was one of the primers used here. Primer MF24 covers nucleotide bases 1231–1247, inclusive, upstream from the beginning of the X ORF, and has the following sequence: 5'AGCGCATGCGTGGAACC3' (SEQ ID NO: 6). Finally, MF31 (residues 1747-1732, SEQ ID NO: 7 5'ccggtaccttACCCCAACTCCTCCCA3 ' ( lower case=kpn1 site added to primer)) and MF24 will be selected for amplification of the X region.

PCR is carried out by extracting HBV DNA from 100 $\mu$of serum. Briefly, serum samples are predigested with DNase I to remove unencapsidated ( and partially degraded) DNA fragments in serum. Samples are then treated with proteinase K, followed by successive extractions with phenol, phenol/chloroform, and chloroform. DNA is recovered by ethanol precipitation in the presence of carrier tRNA, washed, and redissolved in PCR reaction buffer. Preliminary experiments established the optimum conditions for PCR. Amplification is carried out using 1.25 units of Taq polymerase (Perkin Elmer Cetus) per reaction vial . Initial melting is carried out at 95° C. for 5 minutes . After cooling to 7° C., dNTPs and Taq polymerase are added, and 40 cycles carried out under the following conditions: 94° C. for 1 minute (melt) , followed by 55° C. for 1 minute (anneal) , and finally 72° C. for 2 minutes (extend) . At the end of the amplification, the samples are extracted with chloroform, and 10% of the amplified samples analyzed by agarose gel electrophoresis. Positive controls include amplification of serum from hepatitis B e antigen (HBeAg) carriers and from an HBV DNA plasmid. Negative controls include conducting PCR in the presence of extracted nucleic acids from normal human serum, in the presence of no template or irrelevant template, and in the presence of irrelevant primers. Other standard practices related to PCR will be followed to prevent contamination during sample handling.

Example 2 Southern Blot Hybridization

Core region (MFO3+MFO4) amplification products are detected by Southern blot hybridization using a fragment of the core ORF sequences spanning base pairs 1904–2411, inclusive. X region amplification products were detected by using a probe spanning residues 1391–1702. These probes are made by PCR amplification of the cloned HBV DNA with appropriate flanking primers. The fragments were identified by ethidium bromide staining after agarose gel electrophoresis, isolated and labeled with $^{32}P$ by random priming, in accordance with known methods.

Example 3 Assays for anti-HBx and anti-pol

Presence of anti-HBx or anti-pol are determined by coating microtiter wells with selected X antigen or pol antigen derived synthetic peptides, respectively, adding the test serum, and assaying for binding with an enzyme conjugated anti-Ig and substrate. To assay serum samples for anti-HBx, a mixture of synthetic peptides is used to coat microtiter wells (Immunolon 2) overnight at 4° C. Each well contains 1 $\mu$g of each synthetic peptide diluted in 50 $\mu$l of phosphate buffered saline (PBS) containing 0.9% sodium chloride and 10% fetal calf serum (FCS). To assay serum samples for anti-pol, pol peptides are used instead. Following overnight incubation, the wells are washed six times with PBS. The dilutions of test sera (50 $\mu$l/well at 1:10 dilution in PBS/FCS) are then added to the wells, and the plates incubated overnight at 4° C. The wells are then washed six times with PBS. Affinity-purified horseradish peroxidase (HRP)-conjugated goat anti-human Ig (50 $\mu$l/well at 1:100 dilution in PBS/FCS) is added to each well. Plates are incubated for 1 hour at 37° C. and washed six times with PBS, and binding determined colorimetrically with o-phenylenediamine (OPD) at 492 nm. Positive values in each assay are scored as being greater than two standard deviations above the mean of the negative controls. These controls consist of eight human sera negative for serological markers of HBV infection. The specificity of binding for selected anti-HBx [+] sera is determined by preincubating individual serum sample with 25 $\mu$g of each X synthetic peptide for 1 hour at 37° C. before the assay. Similarly, the specificity of the anti-pol assay is determined by adding an analogous preincubation step with an excess of the pol synthetic peptides. In either case, successful blocking is demonstrated by a signal reduction of 50% or more. In addition, sera are tested in wells coated with PBS/FCS (lacking peptides) or in wells coated with irrelevant peptides.

Example 4 DNA Sequence Analysis of a Clone from a Patient with $\beta$Thalassemia A DNA sequence analysis of one clone from a patient with $\beta$-thalassemia was performed. This patient was PCR [+] for the core and X region of HBV DNA, but demonstrated a smear of radioactivity resulting from X plus core amplification, suggesting deletion or alterations within the amplified region. To verify if this was correct, PCR amplification was carried out on a serum sample from this patient with MF24 and MF16, the resulting material cloned into pT7 Blue and one colony analyzed by dideoxy sequencing. A sequence ladder through the region including the deletion is shown in FIG. 4(A). Note that the deletion in this clone spans some of the X promoter/enhancer 1 complex (bases 1322–1375 deleted), most of the X region (bases 1376–1820 deleted; the X gene terminates at base 1838) and the preC translation initiation codon (at position 1816). The point of deletion contains 12 bases whose origin is unknown. FIG. 4(B) is a schematic diagram of the region showing the deleted sequences (dashed lines).

---

What is claimed:

1. A method of detecting hepatitis B variants having deletions within the X region of the virus in a patient sample comprising detecting of antibodies which specifically bind to the polymerase of hepatitis B virus and hepatitis B X antigen in said sample by enzyme linked immunosorbent assays combined with detecting deletions within the X region of the vital genome by polymerase chain reaction using hepatitis B X plus core region primers selected from the group of SEQ ID NO: 4, SEQ ID NO: 5, SEQ ID NO: 6 and SEQ ID NO: 7.

2. A method of screening blood for hepatitis B variants having deletions within the X region of the virus comprising detecting of antibodies which specifically bind to the polymerase of hepatitis B virus and hepatitis B X antigen in said sample by enzyme linked immunosorbent assays combined with detecting deletions within the X region of the vital genome by polymerase chain reaction using hepatitis B X plus core region primers selected from the group of SEQ ID NO: 4, SEQ ID NO: 5, SEQ ID NO: 6, and SEQ ID NO: 7.

* * * * *

UNITED STATES PATENT AND TRADEMARK OFFICE
CERTIFICATE OF CORRECTION

PATENT NO. : 5,378,605

DATED : January 3, 1995

INVENTOR(S) : Feitelson et al.

It is certified that error appears in the above-indentified patent and that said Letters Patent is hereby corrected as shown below:

Column 17, line 39, delete "vital" and insert --viral--.

Column 18, line 38, delete "vital" and insert --viral--.

Signed and Sealed this

Thirtieth Day of May, 1995

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 14
        ( B ) TYPE: Amino Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 1:

```
Leu  Ser  Ala  Met  Ser  Thr  Asp  Leu  Glu  Ala  Tyr  Phe  Lys  Asp
1                   5                         10
```

( 2 ) INFORMATION FOR SEQ ID NO: 2:

( i ) SEQUENCE CHARACTERISTICS:
        ( A ) LENGTH: 14
        ( B ) TYPE: Amino Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 2:

```
Leu  Phe  Lys  Asp  Trp  Glu  Leu  Gly  Glu  Ile  Arg  Leu  Lys  Val
1                   5                         10
```

( 2 ) INFORMATION FOR SEQ ID NO: 3:

( i ) SEQUENCE CHARACTERISTICS:
        ( A ) LENGTH: 10
        ( B ) TYPE: Amino Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 3:

```
Ala  Pro  Ala  Pro  Cys  Asn  Phe  Thr  Ser  Ala
1                   5                         10
```

( 2 ) INFORMATION FOR SEQ ID NO: 4:

( i ) SEQUENCE CHARACTERISTICS:
        ( A ) LENGTH: 28
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 4:

```
ATGGACATCG ACCCTTATAA AGAATTTG                                    2 8
```

( 2 ) INFORMATION FOR SEQ ID NO: 5:

( i ) SEQUENCE CHARACTERISTICS:
        ( A ) LENGTH: 27
        ( B ) TYPE: Nucleic Acid
        ( C ) STRANDEDNESS: Single
        ( D ) TOPOLOGY: Linear (iv) ANTI-SENSE: No (xi) SEQUENCE DESCRIPTION: SEQ ID NO: 5:

CTAAGATTGA GATCTTCTGC GACGCGG  27

(2) INFORMATION FOR SEQ ID NO: 6:

(i) SEQUENCE CHARACTERISTICS:
    (A) LENGTH: 17
    (B) TYPE: Nucleic Acid
    (C) STRANDEDNESS: Single
    (D) TOPOLOGY: Linear (iv) ANTI-SENSE: No (xi) SEQUENCE DESCRIPTION: SEQ ID NO: 6:

AGCGCATGCG TGGAACC  17

(2) INFORMATION FOR SEQ ID NO: 7:

(i) SEQUENCE CHARACTERISTICS:
    (A) LENGTH:
    (B) TYPE: Nucleic Acid
    (C) STRANDEDNESS: Single
    (D) TOPOLOGY: Linear (iv) ANTI-SENSE: No (xi) SEQUENCE DESCRIPTION: SEQ ID NO: 7:

CCGGTACCTT ACCCCAACTC CTCCCA  26